(12) United States Patent
Leung et al.

(10) Patent No.: US 8,343,261 B2
(45) Date of Patent: Jan. 1, 2013

(54) USE OF FORMATE-BASED POROUS METAL ORGANIC FRAMEWORKS FOR METHANE STORAGE

(75) Inventors: Emi Leung, Mannheim (DE); Ulrich Mueller, Neustadt (DE); Gerhard Cox, Bad Duerkheim (DE); Hans Wolfgang Hoeffken, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 304 days.

(21) Appl. No.: 12/921,505

(22) PCT Filed: Mar. 17, 2009

(86) PCT No.: PCT/EP2009/053130
§ 371 (c)(1),
(2), (4) Date: Sep. 8, 2010

(87) PCT Pub. No.: WO2009/115513
PCT Pub. Date: Sep. 24, 2009

(65) Prior Publication Data
US 2011/0178335 A1    Jul. 21, 2011

(30) Foreign Application Priority Data

Mar. 17, 2008   (EP) ..................................... 08152821

(51) Int. Cl.
*B01D 53/02*    (2006.01)
(52) U.S. Cl. .............. 95/141; 95/143; 96/153; 502/400; 502/401; 502/402; 502/439; 502/526
(58) Field of Classification Search ............... 95/90, 141, 95/143, 237; 96/153; 502/400–402, 439, 502/526; 562/609
See application file for complete search history.

(56) References Cited

U.S. PATENT DOCUMENTS

| | | | |
|---|---|---|---|
| 5,264,623 A | | 11/1993 | Oehr et al. |
| 5,998,647 A | | 12/1999 | Seki et al. |
| 7,411,081 B2 | * | 8/2008 | Mueller et al. ................ 556/118 |
| 7,553,352 B2 | * | 6/2009 | Mueller et al. .................... 95/90 |
| 7,815,716 B2 | * | 10/2010 | Mueller et al. .................... 95/90 |
| 2006/0210458 A1 | * | 9/2006 | Mueller et al. ................. 422/231 |
| 2008/0210901 A1 | * | 9/2008 | Giannantonio et al. ... 252/181.5 |
| 2010/0286022 A1 | * | 11/2010 | Yaghi et al. ..................... 514/1.1 |
| 2011/0118490 A1 | * | 5/2011 | Hwang et al. ................... 556/44 |
| 2011/0152375 A1 | * | 6/2011 | Troscher et al. ............... 514/578 |
| 2012/0016066 A1 | * | 1/2012 | Leung et al. ................... 524/284 |
| 2012/0016160 A1 | * | 1/2012 | Leung et al. ................... 562/609 |
| 2012/0055880 A1 | * | 3/2012 | Loiseau et al. ................ 210/660 |

FOREIGN PATENT DOCUMENTS

| | | |
|---|---|---|
| DE | 263 865 | 9/1906 |
| DE | 11 49 674 | 6/1963 |
| EP | 1 674 555 | 6/2006 |
| WO | 2007 118841 | 10/2007 |

OTHER PUBLICATIONS

U.S. Appl. No. 13/003,839, filed Jan. 12, 2011, Schubert, et al.
Rood A. Jeffrey et al., "Synthesis, Structural Characterization, Gas Sorption and Guest-Exchange Studies of the Lightweight, Porous Metal-Organic Framework α-[Mg$_3$(O$_2$CH)$_6$]", Inorganic Chemistry, vol. 45, No. 14, pp. 5521-5528, XP002539785, (2006).

\* cited by examiner

*Primary Examiner* — Duane Smith
*Assistant Examiner* — Christopher P Jones
(74) *Attorney, Agent, or Firm* — Oblon, Spivak, McClelland, Maier & Neustadt, L.L.p.

(57) ABSTRACT

The present invention relates to the use of a porous metal organic framework comprising at least a first organic compound and, if appropriate, a second organic compound, in which at least the first organic compound is at least partially coordinated in a bidentate fashion to at least one metal ion, where the at least one metal ion is Mg(II) and the first organic compound is derived from formic acid and the second organic compound is derived from acetic acid, for storing or isolating methane. Furthermore, the invention relates to a porous metal organic framework based on magnesium formate and acetate and also its preparation.

19 Claims, 3 Drawing Sheets

USE OF FORMATE-BASED POROUS METAL ORGANIC FRAMEWORKS FOR METHANE STORAGE

Figure 1:
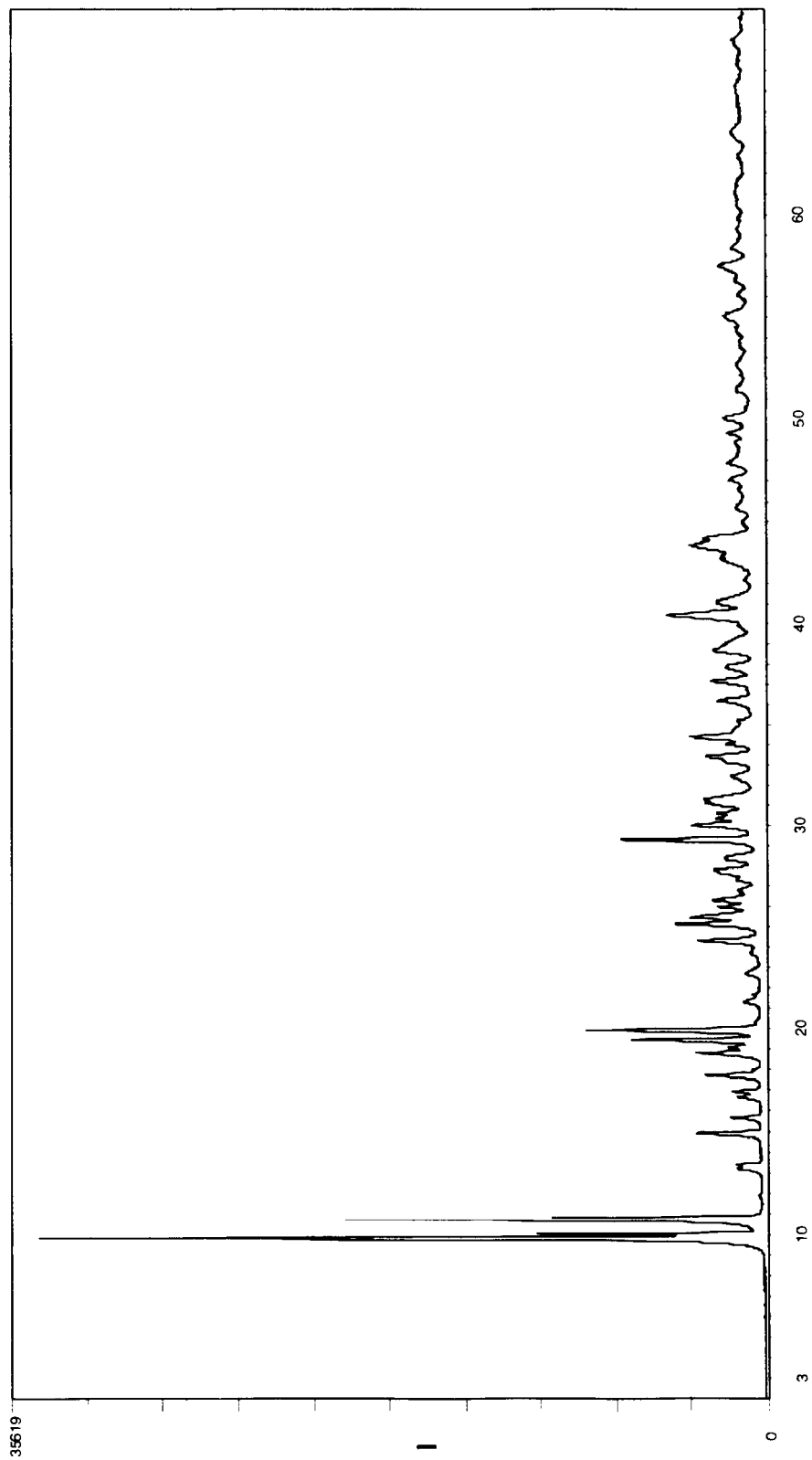

The present invention relates to the use of a porous metal organic framework for storing or separating off methane, corresponding methods, porous metal organic frameworks and their preparation.

Materials for storing or separating gases are known in the prior art. Activated carbons and molecular sieves and also metal organic frameworks may be mentioned by way of example.

The last-named metal organic frameworks, in particular, make it possible to obtain, by appropriate selection of the metal and of the ligand, storage or separation materials which can be used for specific applications.

There is a particular need for inexpensive and robust materials which also display selective behavior in the storage or separation of particular gases.

It has been found in the case of metal organic frameworks that a suitable synthesis makes it possible to obtain frameworks whose constituents are known from conventional salts.

Thus, for example, magnesium formate is commercially available. The dihydrate of magnesium formate, which has the CAS No. 6150-82-9, can, for example, be procured from Sigma Aldrich.

J. A. Rood et al., Inorg. Chem. 45 (2006), 5521-5528, were able to obtain, by means of a suitable synthetic method, a metal organic framework which comprises magnesium and formate and is porous, which was demonstrated by gas adsorption studies using nitrogen and hydrogen.

Despite the metal organic frameworks known in the prior art, there continues to be a need for metal organic frameworks which display, in particular, selective behavior in the storage or separation of particular gases.

It is therefore an object of the present invention to provide suitable uses for storage and separation and also further materials.

The object is achieved by the use of a porous metal organic framework comprising at least a first organic compound and, if appropriate, a second organic compound, in which at least the first organic compound is at least partially coordinated in a bidentate fashion to at least one metal ion, where the at least one metal ion is Mg(II) and the first organic compound is derived from formic acid and the second organic compound is derived from acetic acid, for storing or separating off methane.

The object is also achieved by a porous metal organic framework comprising at least a first organic compound and a second organic compound, in which at least the first organic compound is at least partially coordinated in a bidentate fashion to at least one metal ion, where the at least one metal ion is Mg(II) and the first organic compound is derived from formic acid and the second organic compound is derived from acetic acid.

It has been found that a porous metal organic framework based on magnesium formate is suitable for the storage and separation of methane. Furthermore, it has been found that the preparation of a magnesium formate metal organic framework in the presence of acetic acid makes it possible to obtain a novel metal organic framework whose framework structure is comparable to that of the pure magnesium formate framework and is likewise suitable for storing or separating off methane.

For the purposes of the present invention, the term "derived" means that formic acid and if appropriate acetic acid are present as formate or acetate in the porous metal organic framework according to the present invention, with the partial presence of a protonated form also being possible.

FIG. 1 shows the X-ray diffraction pattern of the metal organic framework according to the invention comprising formate and acetate. In the diffraction pattern, I denotes the intensity ($L_{in}$ (Counts)) and 2Θ denotes the 2-theta scale.

The X-ray diffraction pattern (XRD) of the framework according to the invention preferably displays two reflections in the range 8°<2Θ<12° which are the strongest reflections in the range 2°<2Θ<70°.

The diffraction pattern can be determined as follows: the sample is installed as powder in the sample container of a commercially available instrument (Siemens D-5000 Diffraktometer or Bruker D8-Advance). As radiation source, use is made of Cu-Kα radiation with variable primary and secondary orifice plates and secondary monochromator. The signal is detected by means of a scintillation counter (Siemens) or Solex semiconductor detector (Bruker). The measurement range for 2Θ is typically in the range from 2° to 70°. The angle step is 0.02°, and the measurement time per angle step is typically 2-4 s. In the evaluation, reflections are distinguished from background noise by an at least 3-fold higher signal strength. Area analysis can be carried out manually by drawing a baseline under the individual reflections. As an alternative, it is possible to use programs such as "Topas-Profile" from Bruker, with background matching then preferably being effected automatically by means of a 1st order polynomial in the software.

Furthermore, preference is given to the metal organic framework according to the invention comprising no further metal ions in addition to Mg(II).

In addition, preference is likewise given to the metal organic framework according to the invention comprising no further at least bidentate organic compounds which can coordinate to the at least one metal ion.

The molar ratio of first organic compound to second organic compound in the metal organic framework according to the invention is preferably in the range from 10:1 to 1:10. The ratio is more preferably in the range from 5:1 to 1:5, even more preferably in the range from 2:1 to 1:2, even more preferably in the range from 1.5:1 to 1:1.5, even more preferably in the range from 1.2:1 to 1:1.2, even more preferably in the range from 1.1:1 to 1:1.1 and in particular 1:1. The amounts of formic acid and acetic acid required in the preparation can be used accordingly.

The present invention further provides a process for preparing a porous metal organic framework according to the invention, which comprises the steps (a) reaction of a reaction solution comprising magnesium nitrate hexahydrate, formic acid and acetic acid and also a solvent at a temperature in the range from 110° C. to 150° C. for at least 10 hours and (b) isolation of the precipitated solid.

The process according to the invention for preparing the framework according to the invention comprises, as step (a), the reaction of a reaction solution comprising magnesium nitrate hexahydrate and formic acid, acetic acid and also a solvent at a temperature in the range from 110° C. to 150° C. for at least 10 hours.

The reaction is preferably carried out with stirring for at least part of the time, in particular at the beginning of the reaction.

Magnesium nitrate hexahydrate is used as one starting compound. The initial concentration of this in the reaction solution is preferably in the range from 0.005 mol/l to 0.5 mol/l. The initial concentration is more preferably in the range from 0.1 mol/l to 0.4 mol/l and in particular is in the range from 0.15 mol/l to 0.3 mol/l.

The amount of magnesium nitrate hexahydrate is fed in an amount of the reaction solution, and so the magnesium concentration in the reaction solution decreases as a result of the precipitated solid in step (b).

In addition, the ratio of the initial molar amount of formic acid and acetic acid used to the initial molar amount of magnesium nitrate hexahydrate is preferably in the range from 2.5:1 to 3.0:1. The ratio is more preferably in the range from 2.6:1 to 2.9:1, more preferably in the range from 2.7:1 to 2.8:1. Accordingly, the sum of the initial molar amounts of formic acid and acetic acid has to be considered here.

The reaction solution for step (a) of the method according to the invention for preparing the metal organic framework according to the invention comprises a solvent in addition to magnesium nitrate hexahydrate and formic acid and acetic acid.

The solvent has to be suitable for bringing at least part of the starting materials used into solution. Furthermore, the solvent has to be selected so that the necessary temperature range can be adhered to.

The reaction in the process according to the invention for preparing the material according to the invention is thus carried out in the presence of a solvent. It is possible to use solvothermal conditions here. For the purposes of the present invention, the term "thermal" indicates a preparative process in which the reaction is carried out in a pressure vessel which is closed during the reaction and is heated to an elevated temperature so that pressure builds up within the reaction medium in the pressure vessel as a result of the vapor pressure of the solvent present. In this way, the desired reaction temperature can be achieved if appropriate.

The reaction is preferably not carried out in a water-comprising medium and likewise not under solvothermal conditions.

The reaction in the process according to the invention is accordingly preferably carried out in the presence of a nonaqueous solvent.

The reaction is preferably carried out at a pressure of not more than 2 bar (absolute). However, the pressure is preferably not more than 1230 mbar (absolute). The reaction particularly preferably takes place at atmospheric pressure. However, slightly superatmospheric or subatmospheric pressures can occur as a result of the apparatus. For the purposes of the present invention, the term "atmospheric pressure" therefore refers to the prevailing pressure range from 150 mbar below to 150 mbar above the actual prevailing atmospheric pressure.

The reaction takes place in the temperature range from 110° C. to 150° C. The temperature is preferably in the range from 115° C. to 130° C. The temperature is more preferably in the range from 120° C. to 125° C.

The reaction solution can additionally comprise a base. As a result of the use of an organic solvent, it is frequently not necessary to use such a base. Nevertheless, the solvent for the process according to the invention can be selected so that it itself has a basic reaction, but this is not absolutely necessary for carrying out the process according to the invention.

It is likewise possible to use a base. However, preference is given to no additional base being used.

It is also advantageous for the reaction to be able to take place with stirring, which is also advantageous in a scale-up.

The (nonaqueous) organic solvent is preferably a $C_{1-6}$-alkanol, dimethyl sulfoxide (DMSO), N,N-dimethylformamide (DMF), N,N-diethylformamide (DEF), N,N-dimethylacetamide (DMAc), acetonitrile, toluene, dioxane, benzene, chlorobenzene, methyl ethyl ketone (MEK), pyridine, tetrahydrofuran (THF), ethyl acetate, optionally halogenated $C_{1-200}$-alkane, sulfolane, glycol, N-methylpyrrolidone (NMP), gamma-butyrolactone, alicyclic alcohols such as cyclohexanol, ketones such as acetone or acetylacetone, cyclic ketones such as cyclohexanone, sulfolene or mixtures thereof.

A $C_{1-6}$-alkanol is an alcohol having from 1 to 6 carbon atoms. Examples are methanol, ethanol, n-propanol, i-propanol, n-butanol, i-butanol, t-butanol, pentanol, hexanol and mixtures thereof.

An optionally halogenated $C_{1-200}$-alkane is an alkane which has from 1 to 200 carbon atoms and in which one or more to all hydrogen atoms can be replaced by halogen, preferably chlorine or fluorine, in particular chlorine. Examples are chloroform, dichloromethane, tetrachloromethane, dichloroethane, hexane, heptane, octane and mixtures thereof.

Preferred solvents are DMF, DEF, DMAc and NMP. Particular preference is given to DMF.

The term "nonaqueous" preferably refers to a solvent which has a maximum water content of 10% by weight, more preferably 5% by weight, even more preferably 1% by weight, more preferably 0.1% by weight, particularly preferably 0.01% by weight, based on the total weight of the solvent.

The maximum water content during the reaction is preferably 10% by weight, more preferably 5% by weight and even more preferably 1% by weight.

The term "solvents" refers both to pure solvents and to mixtures of different solvents.

Step (a) of the process according to the invention for preparing the framework according to the invention is carried out for at least 10 hours. The reaction is preferably carried out for at least one day, more preferably at least two days.

The process according to the invention further comprises step (b), viz. isolation of the precipitated solid.

As a result of step (a) of the preparative process according to the invention, the framework precipitates as solid from the reaction solution. It can be isolated by methods known in the prior art, e.g. filtration or the like.

The porous metal organic framework based purely on magnesium formate can be obtained by the above process or by the synthesis described in J. A. Rood et al., Inorg. Chem. 45 (2006), 5521-5528.

Both the metal organic framework based purely on magnesium formate and the magnesium-based porous metal organic framework comprising both formate and acetate can be used for storing and separating off methane. Here, the use of the framework comprising both acetate and formate is preferred.

Accordingly, a preferred embodiment comprises the use of a porous metal organic framework for storing or separating off methane, with the framework comprising the first organic compound and the second organic compound.

A preferred use is separation of methane from a gas mixture by means of a metal organic framework according to the invention.

The gas mixture preferably comprises methane together with carbon monoxide and/or hydrogen.

The present invention further provides the preferred use of the metal organic framework according to the invention and the framework based purely on magnesium formate for separating off methane from a gas mixture comprising methane together with at least one gas selected from the group consisting of carbon monoxide and hydrogen.

On the basis of the abovementioned use of the framework according to the invention and also the framework based purely on magnesium formate, the present invention further provides a method of storing or separating off methane, which comprises the step of contacting of the methane or a methane-comprising gas mixture with an appropriate metal organic framework.

The gas adsorption or separation is in principle carried out according to methods known from the prior art.

Principles and industrial processes are described, for example, in Werner Kast, Adsorption aus der Gasphase, VCH Weinheim, 1988.

Pressure swing adsorption is described, for example, in D. M. Ruthwen et al., Wiley-VCH, 1993.

EXAMPLES

Example 1

Preparation of a Metal Organic Framework Comprising Magnesium Formate Acetate

Starting Materials:

| | | |
|---|---|---|
| 1) Magnesium nitrate*6 H$_2$O | 38.5 mmol | 9.90 g |
| 2) Formic acid | 53.2 mmol | 2.5 g |
| 3) Acetic acid | 53.2 mmol | 3.2 g |
| 4) N,N-Dimethylformamide (DMF) | 2.19 mol | 160.0 g |

The magnesium nitrate is dissolved in DMF in an autoclave liner. A solution of the formic acid and acetic acid is added and the solution is stirred for 10 minutes.
Crystallization:
125° C./78 h
Product Mixture:
Clear solution with white crystals. The solution has a pH of 6.67
Work-Up:
The crystals are filtered off and washed twice with 50 ml of DMF.
Weight: 4.763 g
Solids Content:
Weight: 2.7% of solid FIG. 1 shows the XRD of the material obtained, with I denoting the intensity ($L_{in}$ (counts)) and 2Θ denoting the 2-theta scale.

Example 2

Preparation of a Metal Organic Framework Based on Magnesium Formate

| | | |
|---|---|---|
| 1) Magnesium nitrate*6 water | 38.5 mmol | 9.90 g |
| 2) Formic acid | 106.5 mmol | 4.8 g |
| 3) DMF | 2.19 mol | 160.0 g |

The magnesium nitrate is dissolved in DMF in an autoclave liner. The formic acid is added and the solution is stirred for 10 minutes. (pH=3.49)
Crystallization:
125° C./78 h
Product Mixture:
Clear solution with white crystals Work-Up:
The crystals are filtered off and washed twice with 50 ml of DMF.
Weight: 5.162 g
Solids Content:
Weight: 2.9% of solid Example 3

Adsorption Measurements

Adsorption measurements are carried out on the framework from example 1 and the framework based on magnesium formate from example 2.

Figure 2:
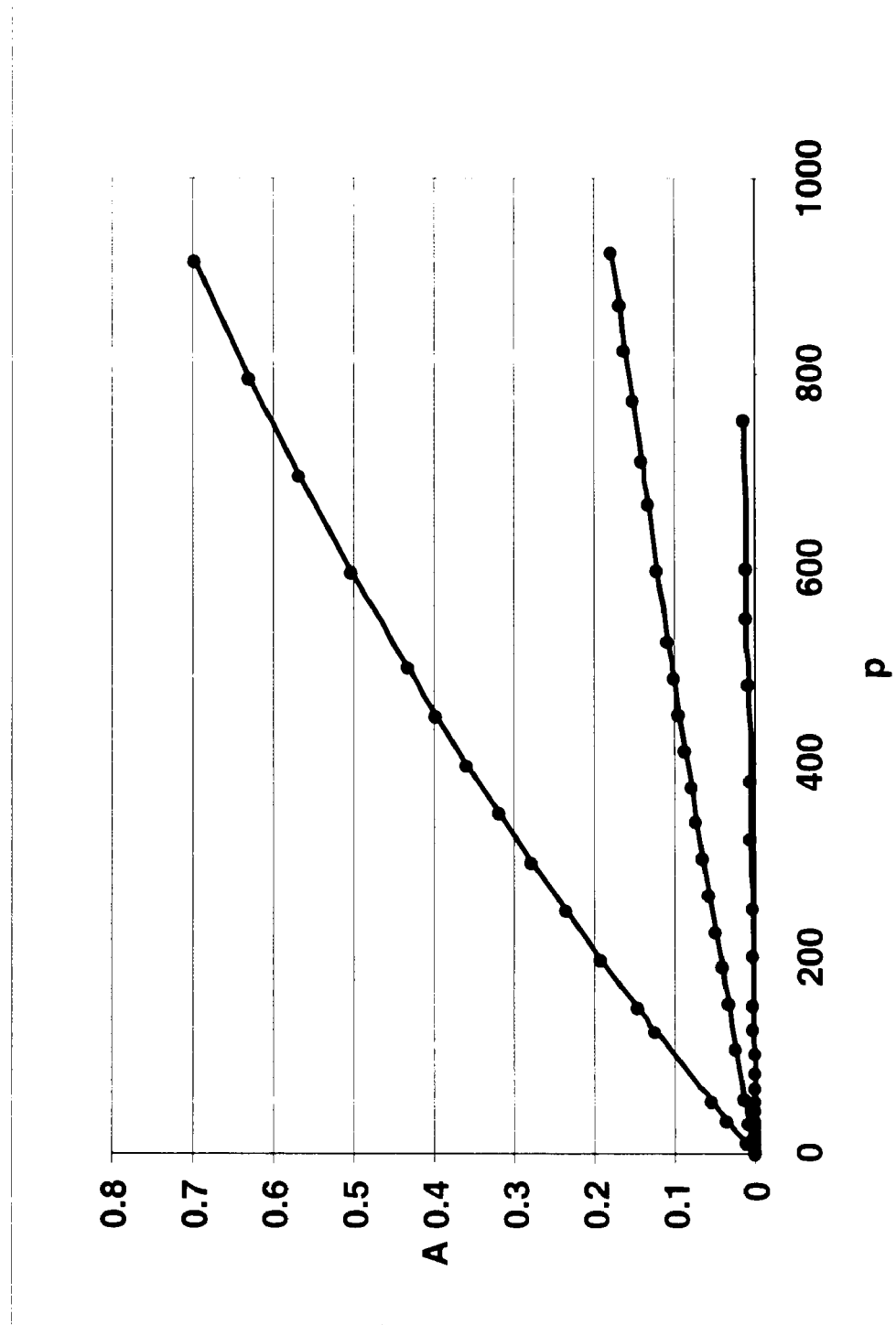

FIG. 2 shows the uptake of methane (upper graph) at 298 K and of carbon monoxide (middle graph) and hydrogen (lower graph) at 313 K for the framework from example 1.

Figure 3:
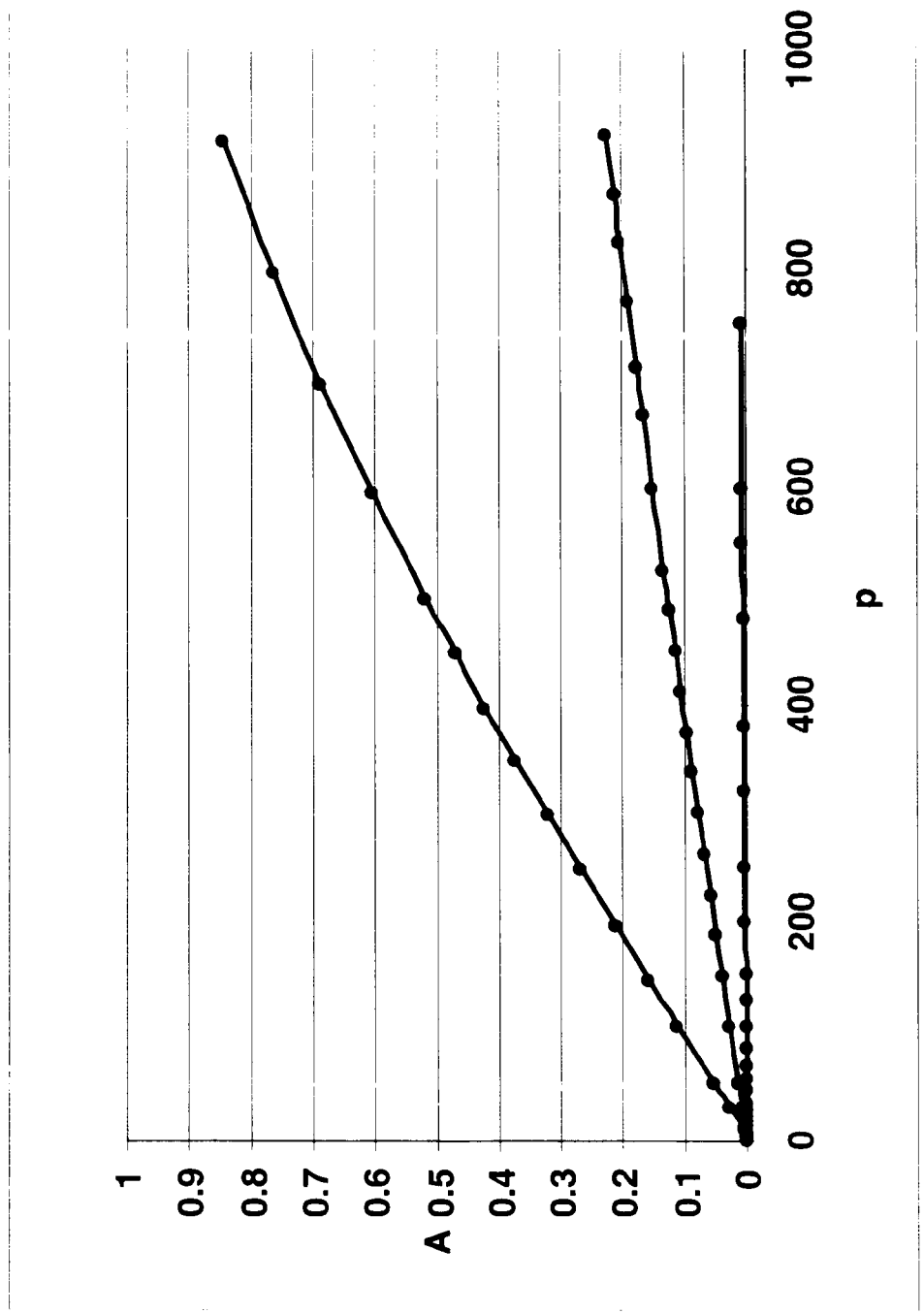

FIG. 3 likewise shows the uptake of methane (upper graph), carbon monoxide (middle graph) and hydrogen (lower graph) by the metal organic framework based on magnesium formate known from the prior art under conditions identical to those maintained in the measurements for FIG. 2.

As can be seen from the isotherms of the pure materials, storage of methane and the separation of methane from a methane-comprising mixture which further comprises carbon monoxide and hydrogen are possible.

FIGS. 2 and 3 show the uptake A (in mmol/g) as a function of the absolute pressure p (in mm of Hg).

The invention claimed is:

1. A method of storing or separating off methane, comprising: contacting the methane or a methane-comprising gas mixture with a porous metal organic framework comprising at least a first organic compound and a second organic compound, in which at least the first organic compound is at least partially coordinated in a bidentate fashion to at least one metal ion, wherein the at least one metal ion is Mg(II) and the first organic compound is derived from formic acid and the second organic compound is derived from acetic acid.

2. The method according to claim 1, wherein methane is separated off from a gas mixture comprising methane together with at least one gas selected from the group consisting of carbon monoxide and hydrogen.

3. The method according to claim 1, wherein methane is separated off from a gas mixture comprising methane together with at least one gas selected from the group consisting of carbon monoxide and hydrogen.

4. The method according to claim 1, wherein first organic compound is formic acid or a formate salt, and the second organic compound is acetic acid or an acetate salt.

5. A porous metal organic framework comprising at least a first organic compound and a second organic compound, in which at least the first organic compound is at least partially coordinated in a bidentate fashion to at least one metal ion, where the at least one metal ion is Mg(II) and the first organic compound is derived from formic acid and the second organic compound is derived from acetic acid.

6. The framework according to claim 5 whose X-ray diffraction pattern (XRD) displays two reflections in a range 8°<2Θ<12° which are the strongest reflections in a range 2°<2Θ<70°.

7. The framework according to claim 6 which comprises no further metal ions in addition to Mg(II).

8. The framework according to claim 7, where a molar ratio of the first organic compound to the second organic compound is in a range from 10:1 to 1:10.

9. The framework according to claim 6, where a molar ratio of the first organic compound to the second organic compound is in a range from 10:1 to 1:10.

10. The framework according to claim 5 which comprises no further metal ions in addition to Mg(II).

11. The framework according to claim 10, where a molar ratio of the first organic compound to the second organic compound is in a range from 10:1 to 1:10.

12. The framework according to claim 5 which comprises no further at least bidentate organic compounds which can coordinate to the at least one metal ion.

13. The framework according to claim 5, where a molar ratio of the first organic compound to the second organic compound is in a range from 10:1 to 1:10.

14. The framework according to claim 5, where a molar ratio of the first organic compound to the second organic compound is in a range from 5:1 to 1:5.

15. The framework according to claim 5, where a molar ratio of the first organic compound to the second organic compound is in a range from 2:1 to 1:2.

16. The framework according to claim 5, where a molar ratio of the first organic compound to the second organic compound is in a range from 1.5:1 to 1:1.5.

17. The framework according to claim 5, where a molar ratio of the first organic compound to the second organic compound is in a range from 1.2:1 to 1:1.2.

18. The framework according to claim 5, where a molar ratio of the first organic compound to the second organic compound is in a range from 1.1:1 to 1:1.1.

19. A process for preparing a porous metal organic framework according to claim 5, the process comprising:
 (a) reacting a reaction solution comprising magnesium nitrate hexahydrate, formic acid, and acetic acid, and also a solvent at a temperature in the range from 110° C. to 150° C. for at least 10 hours; and
 (b) isolating the precipitated solid.

* * * * *